(12) United States Patent
Liu et al.

(10) Patent No.: US 9,320,460 B2
(45) Date of Patent: Apr. 26, 2016

(54) IN-SITU TEAR SAMPLE COLLECTION AND TESTING USING A CONTACT LENS

(71) Applicant: Google Inc., Mountain View, CA (US)

(72) Inventors: Zenghe Liu, Alameda, CA (US); James Etzkorn, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 0 days.

(21) Appl. No.: 14/030,756

(22) Filed: Sep. 18, 2013

(65) Prior Publication Data
US 2014/0194706 A1     Jul. 10, 2014

Related U.S. Application Data

(63) Continuation of application No. 13/606,140, filed on Sep. 7, 2012, now abandoned.

(51) Int. Cl.
*A61B 5/00* (2006.01)
*A61B 5/05* (2006.01)
*A61B 5/145* (2006.01)

(52) U.S. Cl.
CPC .......... *A61B 5/14507* (2013.01); *A61B 5/6821* (2013.01); *A61B 5/14532* (2013.01)

(58) Field of Classification Search
CPC ............. A61B 5/6821; A61B 5/14507; A61B 5/14532
USPC ......... 600/345, 347, 365; 351/159.02, 159.03
See application file for complete search history.

(56) References Cited

U.S. PATENT DOCUMENTS

| | | | |
|---|---|---|---|
| 3,958,560 | A | 5/1976 | March |
| 4,014,321 | A | 3/1977 | March |
| 4,055,378 | A | 10/1977 | Feneberg et al. |
| 4,122,942 | A | 10/1978 | Wolfson |
| 4,136,250 | A | 1/1979 | Mueller et al. |
| 4,143,949 | A | 3/1979 | Chen |
| 4,153,641 | A | 5/1979 | Deichert et al. |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — Christian Jang
(74) *Attorney, Agent, or Firm* — McDonnell Boehnen Hulbert & Berghoff LLP

(57) ABSTRACT

Apparatus, systems and methods employing contact lenses having one or more sensor that sense an analyte in tear fluid and one or more recesses that collect the tear fluid. In some aspects, a contact lens includes a substrate that forms at least part of a body of the contact lens and a recess formed within the substrate configured to collect tear fluid when the contact lens is worn. The contact lens further includes at least one sensor disposed within the substrate configured to sense presence of an analyte in the collected tear fluid.

19 Claims, 11 Drawing Sheets

(56) References Cited

U.S. PATENT DOCUMENTS

| | | |
|---|---|---|
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1* | 1/2007 | Abreu .......................... 600/475 |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |

(56) References Cited

U.S. PATENT DOCUMENTS

| | | | |
|---|---|---|---|
| 2012/0201755 | A1 | 8/2012 | Rozakis et al. |
| 2012/0245444 | A1 | 9/2012 | Otis et al. |
| 2012/0259188 | A1 | 10/2012 | Besling |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| WO | 95/04609 | 2/1995 |
| WO | 0116641 | 3/2001 |
| WO | 01/34312 | 5/2001 |
| WO | 03065876 | 8/2003 |
| WO | 2004/060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010/133317 | 11/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3µW Wirelessly Powered CMOS Glucose Sensor for an Active Contact Lens," 2011 IEEE International Solid-State Circuits Conference, Session 2, Feb. 21, 2011, 3 pages.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Lončar, et al., "Design and Fabrication of Silicon Photonic Crystal Optical Waveguides," Journal of Lightwave Technology, Oct. 2000, vol. 18, No. 10, pp. 1402-1411.

Liu, et al., "Miniature Amperometric Self-Powered Continuous Glucose Sensor with Linear Response," Analytical Chemistry, 7 pages.

Baxter, "Capacitive Sensors," 2000, 17 pages.

Lingley, et al., "A Single-Pixel Wireless Contact Lens Display," Journal of Micromechanics and Microengineering, 2011, 9 pages.

"Polyvinylidene fluoride," Wikipedia, http://en.wikipedia.org/wiki/Polyvinylidene_fluoride, Last accessed Mar. 30, 2012, 4 pages.

Murdan, "Electro-responsive drug delivery from hydrogels," Journal of Controlled Release, 2003, vol. 92, pp. 1-17.

Haders, "New Controlled Release Technologies Broaden Opportunities for Ophthalmic Therapies," Drug Delivery Technology, Jul./Aug. 2009, vol. 8, No. 7, pp. 48-53.

Singh, et al., "Novel Approaches in Formulation and Drug Delivery using Contact Lenses," Journal of Basic and Clinical Pharmacy, May 2011, vol. 2, Issue 2, pp. 87-101.

"Contact Lenses: Look Into My Eyes," The Economist, Jun. 2, 2011, http://www.economist.com/node/18750624/print, Last accessed Mar. 13, 2012, 8 pages.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.

U.S. Appl. No. 13/240,994, Titled "See-Through Display With Infrared Eye-Tracker," filed Sep. 22, 2011, 38 pages Unpublished.

U.S. Appl. No. 13/209,706, Titled "Optical Display System and Method with Gaze Tracking," filed Aug. 15, 2011, 30 pages Unpublished.

Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.

Bull, "Different Types of Statistical Analysis," Article Click, Feb. 4, 2008, 4 pages, http://www.articleclick.com/Article/Different-Types-of-Statistical-Analysis/968252, Last accessed Sep. 4, 2012.

"Understanding pH measurment," Sensorland, 8 pages, http://www.sensorland.com/HowPage037.html, Last accessed Sep. 6, 2012.

"Regression analysis," Wikipedia, 11 pages, http://en.wikipedia.org/wiki/Regression_analysis, Last accessed Sep. 6, 2012.

"Statistics," Wikipedia, 10 pages, http://en.wikipedia.org/wiki/Statistics, Last accessed Sep. 6, 2012.

"Nonlinear regression," Wikipedia, 4 pages, http://en.wikipedia.org/wiki/Nonlinear_regression, Last accessed Sep. 10, 2012.

"Linear regression," Wikipedia, 15 pages, http://en.wikipedia.org/wiki/Linear_regression, Last accessed Sep. 10, 2012.

"Integrated circuit," Wikipedia, 9 pages, http://en.wikipedia.org/wiki/Integrated_circuit, Last accessed Sep. 10, 2012.

"Photolithography," Wikipedia, 8 pages, http://en.wikipedia.org/wiki/Photolithography, Last accessed Sep. 10, 2012.

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

(56) References Cited

OTHER PUBLICATIONS

"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Ho et al., "Contact Lens With Integrated Inorganic Semiconductor Devices," MEMS 2008. IEEE 21st International Conference on. IEEE, 2008., pp. 403-406.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Murdan, "Electro-responsive drug delivery from hydrogels," Journal of Controlled Release, 2003, pp. 1-17, vol. 92.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electra Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-$\mu$W Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Singh, et al., "Novel Approaches in Formulation and Drug Delivery using Contact Lenses," Journal of Basic and Clinical Pharmacy, May 2011, pp. 87-101, vol. 2, Issue 2.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 $\mu$A, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

\* cited by examiner

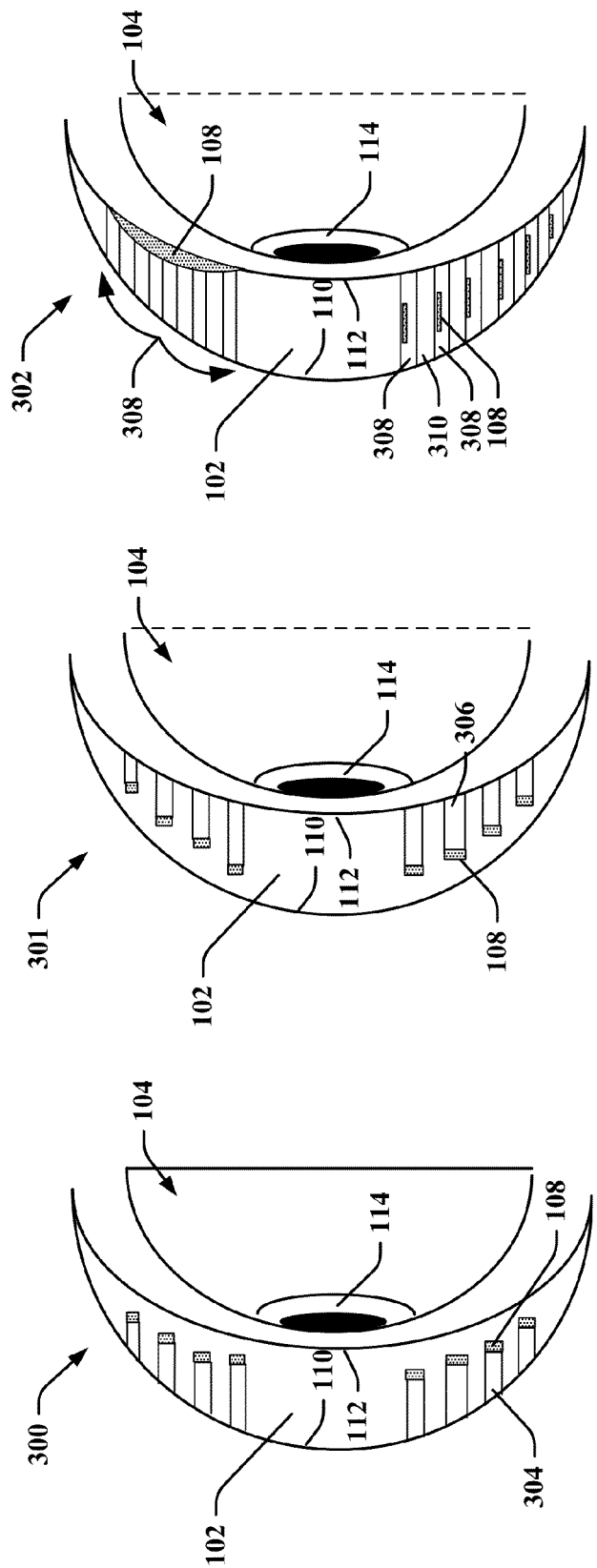

US 9,320,460 B2

IN-SITU TEAR SAMPLE COLLECTION AND TESTING USING A CONTACT LENS

CROSS REFERENCE TO RELATED APPLICATIONS

The present application is a continuation of U.S. patent application Ser. No. 13/606,140, filed Sep. 7, 2012, which is currently pending. The entire disclosure contents of this application are herewith incorporated by reference into the present application.

TECHNICAL FIELD

This disclosure generally relates to a contact lens employing one or more recesses integrated within a substrate that collect tear fluid and supply collected tear fluid to a sensor for sensing of an analyte therein.

BACKGROUND

Tear fluid provides a viable source of biological analytes that can indicate various health states of an individual from which tear fluid is generated. However, collection of tear samples for testing is difficult. Many processes for collecting tear samples usually irritate the eye and produce tear fluid having constituents which can lead to erroneous test results. For example, tear fluid generated from irritation of an eye, such as touching of the eye and tear fluid generated from an emotional reaction comprise different constituents than basal tears and are generally produced in greater quantity than basal tears. Such reflex and emotional tears interfere with composition of tear samples of interest.

In order to avoid some of the aforementioned drawbacks associated with collection of tear fluid, contact lenses have been established that employ internal sensing platforms for in-situ testing of tear fluid for analytes. These contact lenses generally test tear fluid that forms a tear film over the contact lens. However, the total volume of tear fluid establishing the tear film is often insufficient for in-situ testing of various analytes.

BRIEF DESCRIPTION OF THE DRAWINGS

FIG. 3A-3C illustrate examples contact lens having a plurality of recesses for collecting tear fluid and/or having a plurality of sensors for sensing one or more analytes in the collected tear fluid in accordance with aspects described herein.

DETAILED DESCRIPTION

Figure 1:
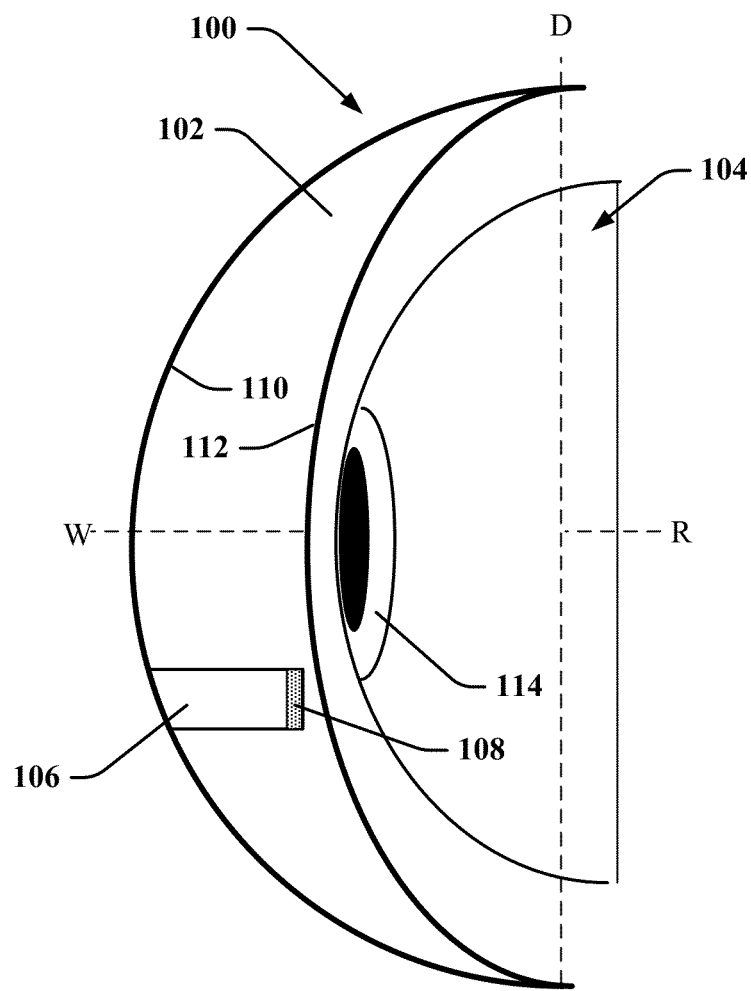
FIG. 1 illustrates an example contact lens having a recess for collecting tear fluid and having a sensor for sensing an analyte in the collected tear fluid in accordance with aspects described herein.

In one or more aspects, the disclosed subject matter relates to a contact lens that facilitates in-situ tear fluid testing. In some aspects, the contact lens includes a substrate that forms at least part of a body of the contact lens and a recess formed within the substrate configured to collect tear fluid when the contact lens is worn. The contact lens further includes at least one sensor disposed within the substrate configured to sense presence of an analyte in the collected tear fluid.

In another aspect, a method is disclosed that includes collecting tear fluid in a cavity disposed within a body of a contact lens and detecting presence of at least one analyte in the collected tear fluid via at least one sensor located within the body of the contact lens. In one aspect, the at least one sensor is located within the cavity. In another aspect, the at least one sensor is located adjacent to the cavity and the cavity includes an opening through which the tear fluid contacts the at least one sensor. According to this aspect, the method can include dispensing a portion of the tear fluid from the cavity via the opening so that the portion of the tear fluid contacts the at least one sensor.

In another embodiment, a contact lens is provided having a tear fluid collection recess formed in a substrate that forms at least part of a body of the contact lens and configured to collect tear fluid when the contact lens is worn. The contact lens further includes at least one sensor configured to sense presence of one or more analytes the tear fluid and a processor configured to determines or infer type or concentration of the one or more analytes. A transmitter is also included on or within the contact lens configured to transmit information relating to type or concentration of the one or more analytes to an external device.

Various aspects are now described with reference to the drawings, wherein like reference numerals are used to refer to like elements throughout. It should be appreciated that one or more aspects of the drawings from are not drawn to scale. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

With reference now to the drawings, FIG. 1 illustrates a cross-sectional view of an example tear fluid collecting contact lens 100 in accordance with aspects described herein. Contact lens 100 includes a recess or cavity 106 for collecting tear fluid and having a sensor 108 for sensing an analyte in the collected tear fluid when the contact lens 100 is worn over an eye 104. As used herein the terms recess and cavity are used interchangeably. The recess 106 is configured to collect tear fluid over time as the contact lens 104 is worn over an eye. In an aspect, the recess 106 collects tear fluid via capillary action and/or osmosis. The collected tear fluid serves as a reservoir of tear fluid for analyte sensing processes of sensor 108.

In particular, tear fluid provides a viable source of biological analytes that can indicate various health states of the individual from which the tear fluid is generated. Contact lenses having integrated sensors for sensing various analytes generally test analytes present in tear fluid that forms a tear film over the contact lens. However, the total volume of tear fluid establishing the tear film is often insufficient for in-situ testing of various analytes. For example, electrochemical sensors can be employed within a contact lens that perform oxidation or reduction of an analyte of interest and measure current generated in association with oxidation or reduction. However, when to ear film serves as a sole source of analyte, continuous sensing by an electrochemical sensor is often compromised because the limited amount of analyte in the tear film can be quickly consumed by the sensor.

Contact lens 100 is depicted having a single cavity 106. However in various aspects, contact lenses disclosed herein can include any suitable number N of cavities, N is an integer. Cavities, such as cavity 106 provided within the disclosed tear fluid collecting contact lenses, such as contact lens 100, can fill with tear fluid over a period of time dependant on size and shape of cavities. Further, tear collecting cavities provided within contact lenses disclosed herein can slowly fill with tear fluid over time so as not to dry out an eye. It is to be appreciated that the contact lens can be designed and configured to collect tear fluid over any suitable range of time (e.g., seconds, minutes, hours, days, weeks, or months). In an aspect, the cavities are configured to store collected tear fluid while the contact lens is worn in the eye, and when the contact lens is removed from the eye.

As illustrated in FIG. 1, cavity 106 and sensor 108 are located within a body or substrate 102 of the contact lens 100. In an aspect, the substrate 102 is a hydrogel—the contact lenses disclosed herein can comprise any suitable material that can be employed to create one or more tear collecting cavities within the substrate 102. In an aspect, the contact lenses disclosed herein can include soft lenses made from one or more soft polymer materials including but not limited to, a hydrogel, a silicone based hydrogel, a polyacrylamide, or a hydrophilic polymer. For example, in an aspect, contact lenses disclosed herein can include crosslinked hydrogels including hydrophilic monomers (e.g. N-Vinylpyrrolidone, N,N-dimethylacrylamide, 2-hydroxyethyl methacrylate, hydroxyethyl acrylate, methacrylic acid and acrylic acid), strengthening agents, ultraviolet light (UV) blockers, or tints. In another aspect, contact lenses disclosed herein can include silicone hydrogels (e.g. crosslinked hydrogels containing silicone macromers and monomers, as well as hydrophilic monomers that absorb water). In yet another aspect, contact lenses disclosed herein can include hard lenses made from one or more rigid materials including but not limited to, a silicone polymer, polymethyl methacrylate, or rigid gas permeable materials.

Although not to be limited to such shape, the contact lenses disclosed herein, such as contact lens 100, are generally provided in a spherical shape that conforms to shape of an eye. With reference to FIG. 1, contact lens 100 include two primary surfaces, an inner surface 112 and an outer surface 110, both of which are spherical. The inner surface 112 is concave and is shown facing and resting on a surface of the eye 104, and conforming to shape of cornea 114—the outer surface 110 is convex.

In an aspect, as depicted in FIG. 1, a cavity 106 is located within the substrate 102 and adjacent outer wall 112. According to this aspect, cavity 106 is designed to collect tear fluid disposed on the outer surface of the contact lens 102. It is to be appreciated that cavity 106 includes an opening or diffusion layer adjacent the outer surface 110 of the contact lens at which tear fluid enters via capillary action and/or osmosis respectively. In other aspects, tear collecting cavities are disposed within the substrate 102 and adjacent to the inner surface 112 or a perimeter edge of the contact lens 100. Regardless of location of a cavity within the substrate, the respective cavity includes an opening and/or diffusion layer adjacent to a surface of the contact lens that facilitates influx of tear fluid.

In an aspect, a cavity 106 can be located within the substrate at or near a perimeter of the substrate so that the cavity is not located in front of the cornea 114 of the eye when the contact lens in worn in the eye. According to this aspect, a cavity provided within the substrate of a contact lens can have a length slightly less than a radius (midway point R of FIG. 1) of the contact lens. However a cavity may be provided within a contact lens having a length that ranges substantially the length or diameter (dashed line D) of the substrate.

Cavities disposed within the disclosed contact lenses, such as cavity 106 of contact lens 100, can have any suitable size and shape that facilitate collection of tear fluid without irritating the eye, without disrupting the functions of the eye, without disrupting function of the contact lens, and without causing discomfort to the wearer. For example, cavity 106 can have a rectangular shape (as depicted in FIG. 1), a cylindrical shape, or a semi-ellipsoid shape. In various aspects, cavity 106 has an optimal size that facilitates collecting an amount of tear fluid for performing continuous sensing by a sensor 108 when the tear fluid is provided to the sensor 108. Accordingly, the size and shape of a cavity can vary depending on functions of sensor 108 that will be sensing the tear fluid collected within the cavity.

Contact lens 100 (and additional contact lenses described herein) has a thickness or width that spans in a horizontal direction between inner surface 112 and outer surface 110. In general aspects, the width of the lens is thickest (relative to the width of the lens at other areas of the lens) at the center point of the lens, tapering outwardly to a knifelike edge at the perimeter of the lens. Dashed line W indicates direction of the width or depth of the contact lens 100. The diameter of the contact lens 100 is indicated by dashed line D. The particular dimensions (including dimensions attributable to thickness, diameter, curvature, and etc.) of the subject contact lenses are not critical and may vary.

In an aspect, a cavity, such as cavity 106 provided within the substrate of a contact lens, such as contact lens 100, can have a depth that spans within the thickness or width W of the substrate, including the entire thickness. For example, the thickness or width of the substrate of a contact lens can range about 1.0 μm to about 400 μm depending on type of lens and distance from center point. Generally, contact lenses have a thickness of about 50 µm to about 150 µm. In typical human eyes, the tear film has a general thickness of about 7-8 µm while the total volume of tears in an eye is about 6-8 µL. With this in mind, for every 10 µm of depth of a tear collecting cavity (e.g. cavity 106), available volume of tears for consumption by a sensor within the contact lens (e.g. sensor 108) can be doubled as compared to available tears in regular tear film.

In an aspect, where the substrate has a thickness of about 400 µm, a cavity can have a width or depth of about 400 µm or less and about 10 µm, more particularly, a depth of about 150 µm or less and about 25 µm, and even more particularly, a depth of about 100 µm or less and about 50 µm. In another aspect, where the substrate has a thickness of about 150 µm, a cavity can have a width or depth of about 150 µm or less and about 10 µm, more particularly, a depth of about 100 µm or less and about 25 µm, and even more particularly, a depth of about 75 µm or less and about 50 µm.

In an embodiment, cavities provided within the subject tear collecting contact lenses are considered microcavities. The term microcavity as used herein includes cavities, channels, cells, or other cavity capable of collecting and storing tear fluid having a volumetric size less than the entire volume of the substrate in which it is located. In an aspect, the total volume of the contact lens substrate is about 25 to about 50 micro liters. With this in mind, in an aspect, a microcavity has a volume less than about 50% of the total volume of the substrate. In another aspect, a microcavity has a volume less than about 25% of the total volume of the substrate. In another aspect, a microcavity has a volume less than about 10% of the total volume of the substrate. In yet another aspect, a microcavity has a volume less than about 5% of the total volume of the substrate. In yet another aspect, a microcavity has a volume less than about 0.1% of the total volume of the substrate. Still in yet another aspect a microcavity has a volume less than about 0.01% of the total volume of the substrate.

Referring back to FIG. 1, contact lens 100 (and additional contact lenses described herein) includes a sensor 108 configured to sense one or more analytes within tear fluid collected in cavity 106. In an aspect, as illustrated in FIG. 1, the sensor 108 is located within cavity 106. Sensor 108 and additional sensory employed in contact lenses disclosed herein, can include a variety of sensors configured to sense one or more analytes of interest. For example, sensors for employment with the disclosed contact lenses can include but are not limited to, an electrochemical sensor, a biosensor, an amperometric sensor, or a pressure sensor. Such sensors can be configured to sense information indicative of presence and/or concentration of various analytes in collected tear fluid, including but not limited to glucose, alcohol, histamine, urea, lactate, cholesterol, or electrolyte ions such as sodium, potassium, calcium and magnesium. In an aspect, sensor 108 can include two or more sensors configured to sense different analytes of interest.

Figure 2B:
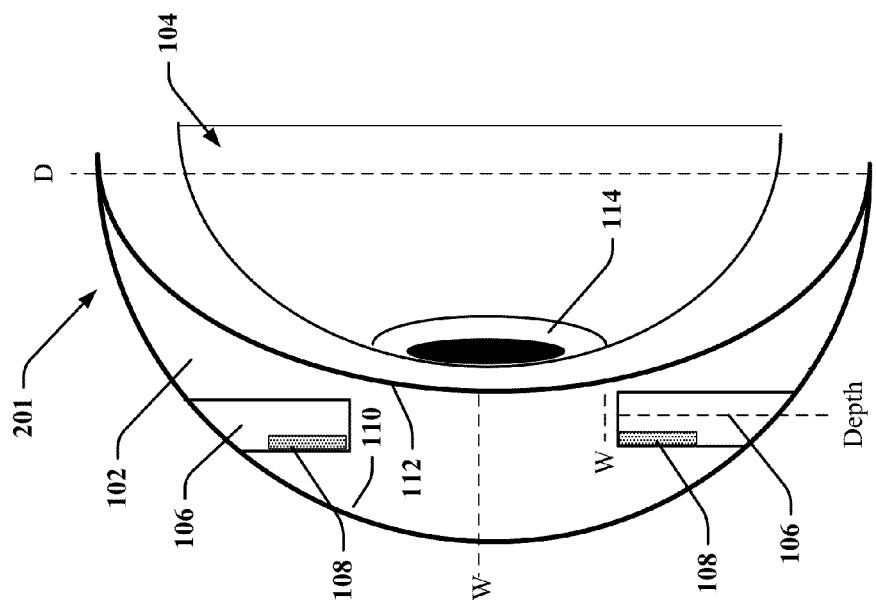
FIGS. 2A and 2B illustrate additional examples of contact lenses having one or more recesses for collecting tear fluid and having a sensor for sensing an analyte in the collected tear fluid in accordance with aspects described herein.
Figure 2A:
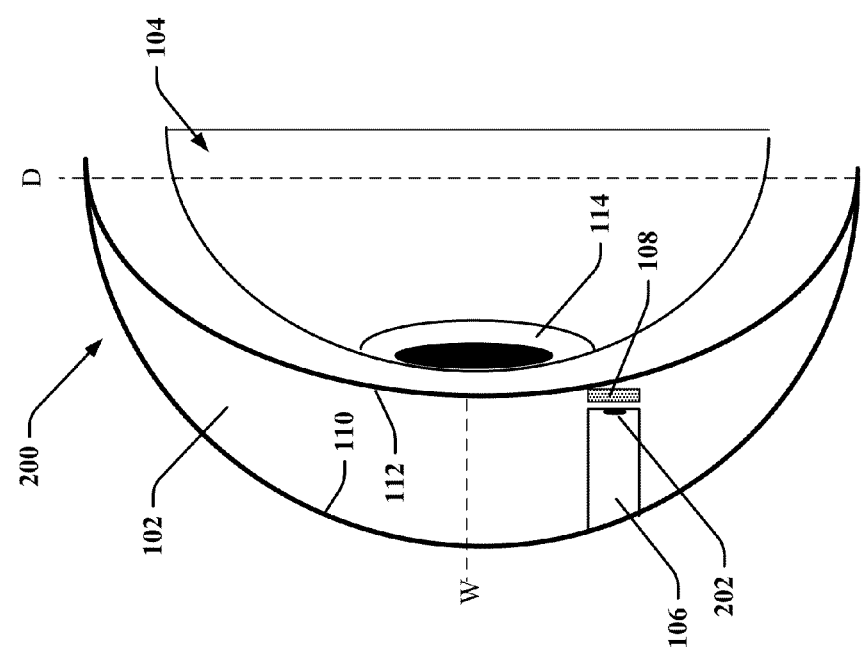

Turning now to FIG. 2A presented is another cross-sectional view of an example tear fluid collecting contact lens 200 in accordance with aspects described herein. Contact lens 200 includes a recess or cavity 106 for collecting tear fluid and having a sensor 108 for sensing an analyte in the collected tear fluid when the contact lens 200 is worn over an eye 104. Repetitive description of like elements employed in respective embodiments of contact lenses described herein is omitted for sake of brevity.

Contact lens 200 is similar to contact lens 100 with the exception that sensor 108 is located within the substrate 102 yet outside of cavity 106. According to this embodiment, cavity 106 can include an opening and/or a diffusion layer 202 configured to release or excrete collected tear fluid. For example, the opening 202 can include a relatively small hole through which collected tear fluid slowly and steadily escapes cavity 106 in a controlled fashion. The size and shape of the opening 202 can be selected such that a predetermined amount of tear fluid is dispensed from cavity 106 at a predetermined rate. In aspect, rather than a hole, cavity 106 can include a diffusion layer 202 that includes a material that allows for the diffusion of tear fluid out of cavity 106. The diffusion layer material can be selected such that a predetermined amount of tear fluid is dispensed from cavity 106 at a predetermined rate.

According to this embodiment, sensor 108 is provided within the substrate 102 outside of cavity 106 and substantially adjacent to opening 108. As tear fluid is dispensed through opening 108, it contacts sensor 108. With this configuration, sensor 108 can be provided a controlled amount of fresh tear fluid at a continuous rate. In an aspect, by separating sensor 108 from the reservoir of tear fluid collected in cavity 106, by-products generated by the sensor 108 can be separated from the collected tear fluid so as to not contaminate the collected tear fluid. In addition, by providing sensor 108 with a continuous supply of fresh tear fluid, changes in the analyte composition of the tear fluid over time can be more accurately discerned.

FIG. 2B presents another cross-sectional view of an example tear fluid collecting contact lens 201 in accordance with aspects described herein. Contact lens 201 includes a recess or cavity 106 for collecting tear fluid and having a sensor 108 for sensing an analyte in the collected tear fluid when the contact lens 201 is worn over an eye 104.

Contact lens 201 is similar to contact lens 100 with exception of inclusion of two or more cavities 106 provided within the substrate and disposition of cavities 106 and sensors 108 within the substrate 102. According to this embodiment, cavity 106 is disposed within the substrate 102 such that depth of the cavity spans substantially parallel with diameter D of the substrate. Cavities 106 are adjacent to outer surfaces 110 of the substrate 102 towards an outer perimeter of the contact lens. In particular, a cavity 106 has a width W that spans within the thickness of the substrate, substantially perpendicular to the inner 112 and outer 110 surfaces of the substrate, and a depth greater than the width that spans substantially parallel to the inner 112 and outer 110 surfaces of the substrate. With this embodiment, depth of cavity 106 can be increased to a depth greater than thickness of the substrate. It should be appreciated that cavities 106 are depicted having a rectangular shape merely for illustrative purposes, and are not to be limited to such shape or configuration. For example, cavities 106 can have a shape that substantially corresponds to the curvature of the contact lens 201. Sensors 108 can be further located within cavities 106 and adjacent to a side surface of the respective cavities.

FIG. 3A presents another cross-sectional view of an example tear fluid collecting contact lens 300 in accordance with aspects described herein. Contact lens 300 includes a plurality of cavities 304 for collecting tear fluid. Respective cavities 304 are further associated with respective sensors 108 for sensing an analyte in the collected tear fluid when the contact lens 300 is worn over an eye 104.

Contact lens 300 is depicted having eight cavities 304, however it should be appreciated that contact lens 300 can include any number N cavities. Respective cavities 304 are disposed within the substrate adjacent to outer surface 110 of the contact lens 300. According to this aspect, cavities 304 can collect tear fluid disposed on the outer surface 110 of the contact lens. Sensors 108 can be located within the cavities 304 and/or outside the cavities, (as depicted in FIGS. 1 and 2A respectively). In an aspect, respective sensors 108 associated with the respective cavities 304 are configured to sense presence and/or concentration of different analytes. Therefore, contact lens 300 can sense information associated with a plurality of different analytes at the same time while sensing mechanisms of the respective sensors 108 do not interfere with one another. For example, by-products of a first reaction associated with a first sensor can be contained within a first cavity. As a result, the by-products of the first reaction will not interfere with sensing mechanisms of a second sensor disposed within a second cavity and configured to perform a different reaction with respect to a different analyte of interest.

FIG. 3B presents another cross-sectional view of an example tear fluid collecting contact lens 301 in accordance with aspects described herein. Contact lens 301 includes a plurality of cavities 306 for collecting tear fluid. Respective cavities 306 are further associated with respective sensors 108 for sensing an analyte in the collected tear fluid when the contact lens 301 is worn over an eye 104. Contact lens 301 is similar to contact lens 300 with exception of disposition of cavities 306 within the substrate 102. In particular, with contact lens 301, the cavities 306 are located adjacent to an inner surface 112 of the substrate 102. According to this aspect, the cavities 306 can collect tear fluid present on an inner surface 112 of the contact lens and/or a surface of the eye 104.

FIG. 3C presents another cross-sectional view of an example tear fluid collecting contact lens 302 in accordance with aspects described herein. Contact lens 302 includes a plurality of cavities 308 for collecting tear fluid. In one aspect, respective cavities 308 are further associated with respective sensors 108 for sensing an analyte in the collected tear fluid when the contact lens 302 is worn over an eye 104 (as depicted in the lower half of contact lens 302). In another aspect, a plurality of cavities 308 can share a single sensor 108 (as depicted in the upper half of contact lens 302).

Contact lens 302 is similar to contact lens 300 with exception of disposition of cavities 308 and/or one or more sensors 108 within the substrate 102. In particular, cavities 308 span an entire width or thickness of contact lens 302. Cavities 308 can include an opening adjacent to an inner surface 112 and/or an outer surface 110 of the substrate 102. In an aspect, as presented in the lower half of contact lens 302, a plurality of cavities 308 span the thickness of the substrate and are separated from one another by a space 310. Respective cavities 308 in the lower half of the contact lens 302 further include a sensor 108 located therein. In another aspect, as depicted in the upper half of contact lens 302, a plurality of cavities are provided adjacent to one another and span the thickness of the substrate. Further, the plurality of cavities 308 in the upper half of contact lens 302 can share a single sensor 108. In an aspect, the shared sensor is located just outside/external to the plurality of cavities. In another aspect, the shared sensor is located within the plurality of cavities 308.

Figure 4B:
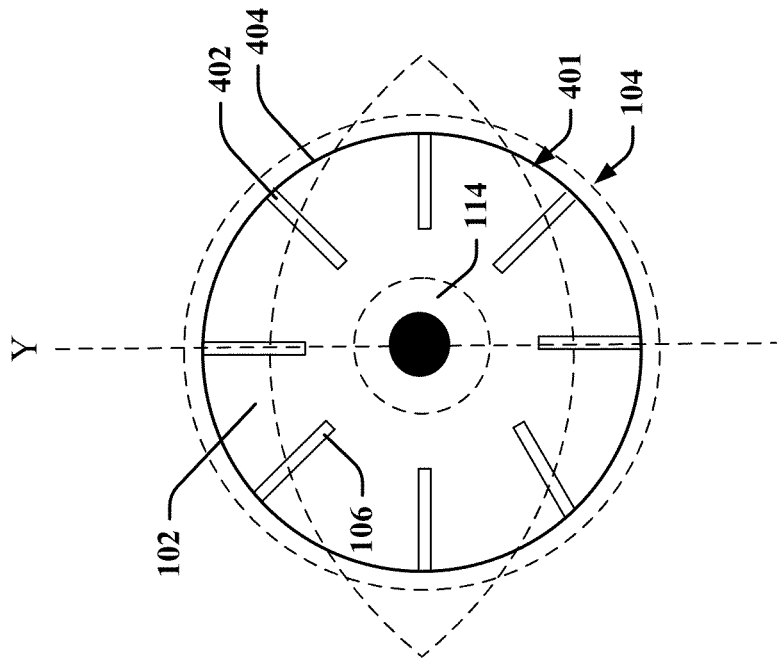
FIG. 4A-4B illustrate top planar views of examples of contact lenses having a plurality of recesses for collecting tear fluid and having a sensor for sensing an analyte in the collected tear fluid in accordance with aspects described herein.
Figure 4A:
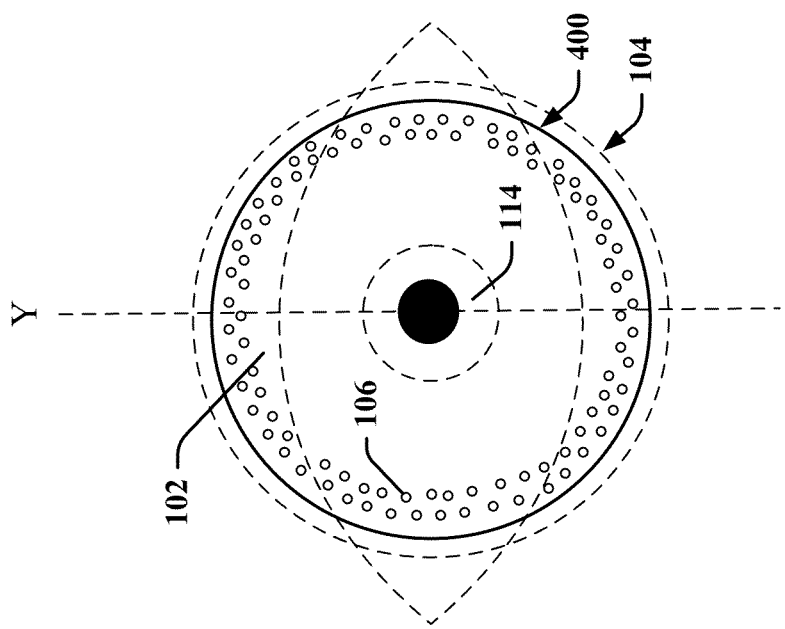

Referring now to FIGS. 4A and 4B, depicted are top planar views of example contact lenses 400 and 401, respectively, worn over an eye 104 in accordance with aspects described herein. In an aspect, lenses 300302 can have top planar configurations same or similar to that depicted of lens 400. In particular, the cross-section of lens 400 taken along axis Y can resemble the cross-sections of lenses 300301, where the cavities 106 of lens 400 and similarly lenses 300301 are provided having a depth/length that spans the width of the substrate (e.g. substantially perpendicular to a surface of the lens). It should be appreciate that the number of cavities 106 depicted and proportional size of the cavities shown is not limiting and is merely intended for illustrative purposes. For example, lens 400 can have any number N of cavities (where N is an integer) of varying size. The cavities 106 of lens 400 are located within the substrate 102 and are disposed a radial distance away from the center of the lens so as not to cover the cornea 114 of the eye.

With reference to FIG. 4B, presented is another top-planar view of an example tear collecting contact lens 401 in accordance with disclosed aspects. In an aspect, lens 401 demonstrates a potential top planar configuration of contact lens 201. In particular, the cross-section of lens 401 taken along axis Y can resemble the cross-section of lens 202, where the cavities 106 of lens 401 and similarly lens 202, are provided having a depth/length that spans a length of the substrate (e.g. substantially parallel to a surface of the lens). It should be appreciated that number of cavities 106 depicted and proportional size of the cavities depicted (e.g. eight) is not limiting and is merely intended for illustrative purposes. For example, lens 401 can have any number N of cavities (where N is an integer) of varying size. The cavities 106 of lens 401 are located within the substrate 102 and are disposed a radial distance away from the center of the lens so as not to cover the cornea of the eye (e.g. the pupil 112 and the iris 114). In an aspect, cavities 106 can have respective openings 402 at an outer edge/perimeter 404 of the lens 401.

Figure 5:
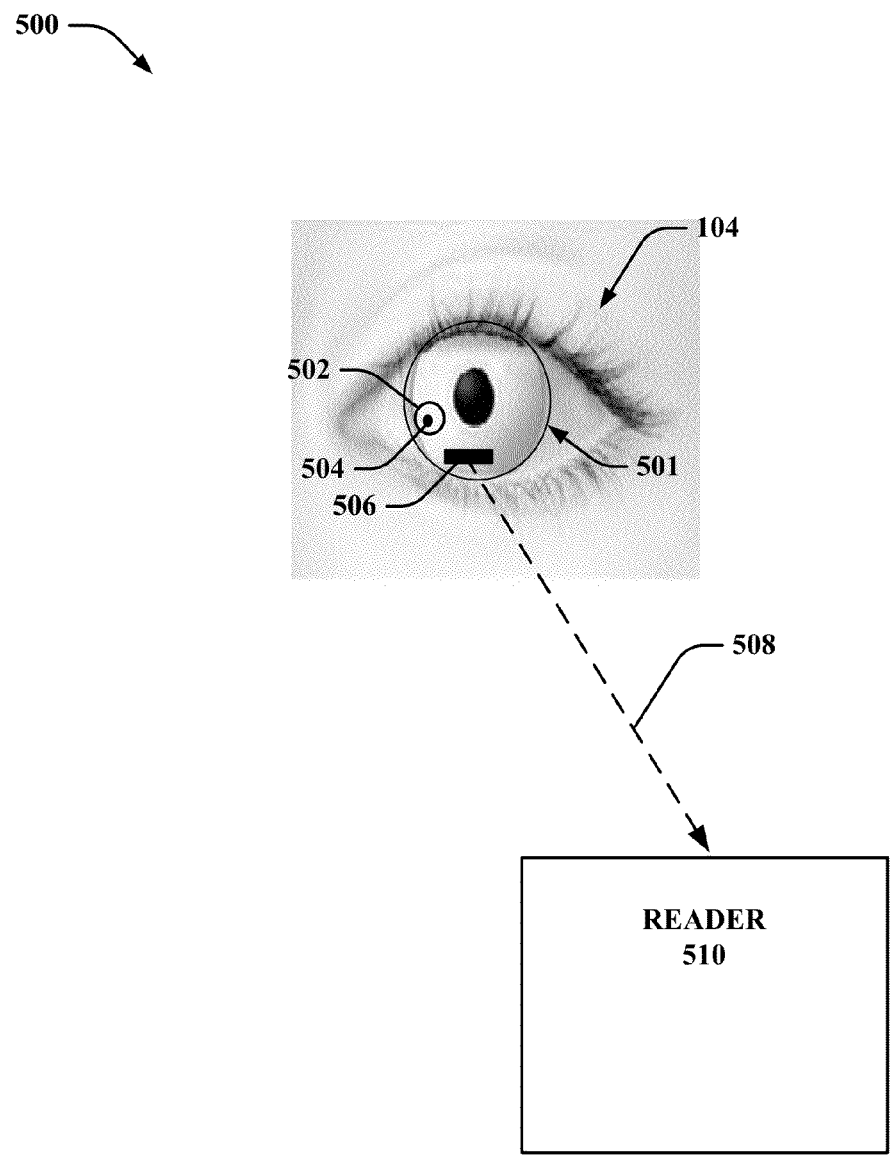
FIG. 5 presents an illustration of an exemplary non-limiting system that includes a contact lens that facilitates sensing and determining information associated with an analyte present within tear fluid generated by a wearer of the contact lens in accordance with aspects described herein.

With reference now FIG. 5, presented is a depiction of system 500 that includes a contact lens 501 that facilitates sensing and determining information associated with an analyte present within tear fluid generated by a wearer of the contact lens 501 in accordance with aspects described herein. Contact lens 501 covers at least a portion of an eye 104. Contact lens 501 includes one or more recesses 502 configured to collect tear fluid and one or more sensors 504 configured to sense presence and/or concentration of an analyte of interest in the collected tear fluid. Repetitive description of like elements employed in respective embodiments of contact lenses described herein, such as sensors and/or recesses is omitted for sake of brevity.

Contact lens 501 further includes a contact lens circuit 506 that facilitates sensing functions of the one or more sensors 504, analyzing information sensed by the one or more sensors 504, and wirelessly communicating information associated with information sensed by the one or more sensors 504. One or more components of contact lens circuit 506 can be communicatively coupled to the one more sensors 504 (e.g. using one or more wires and/or chemically). Contact lens circuit 506 is described in greater detail with reference to FIG. 6.

In an aspect, contact lens circuit 506 includes various electrical and/or machine based components that facilitate gathering information sensed by the one or more sensors 504, analyzing the information, and/or transmitting the information to an external reader device 510. In an aspect, the contact lens circuit 506 includes at least a communication component (not shown) configured to wirelessly transmit data associated with information sensed by the one or more sensors 504. For example, such information can include data indicating presence and/or concentration of an analyte present within tear fluid generated by the wearer of lens 501 and collected in the one or more cavities 502. In an aspect, the communication component can include an antenna, such as a radio frequency (RF) antenna configured to transmit the information using a radio wave. In another aspect, the communication component can include one or more LEDs configured to transmit the information using light signals.

Figure 6:
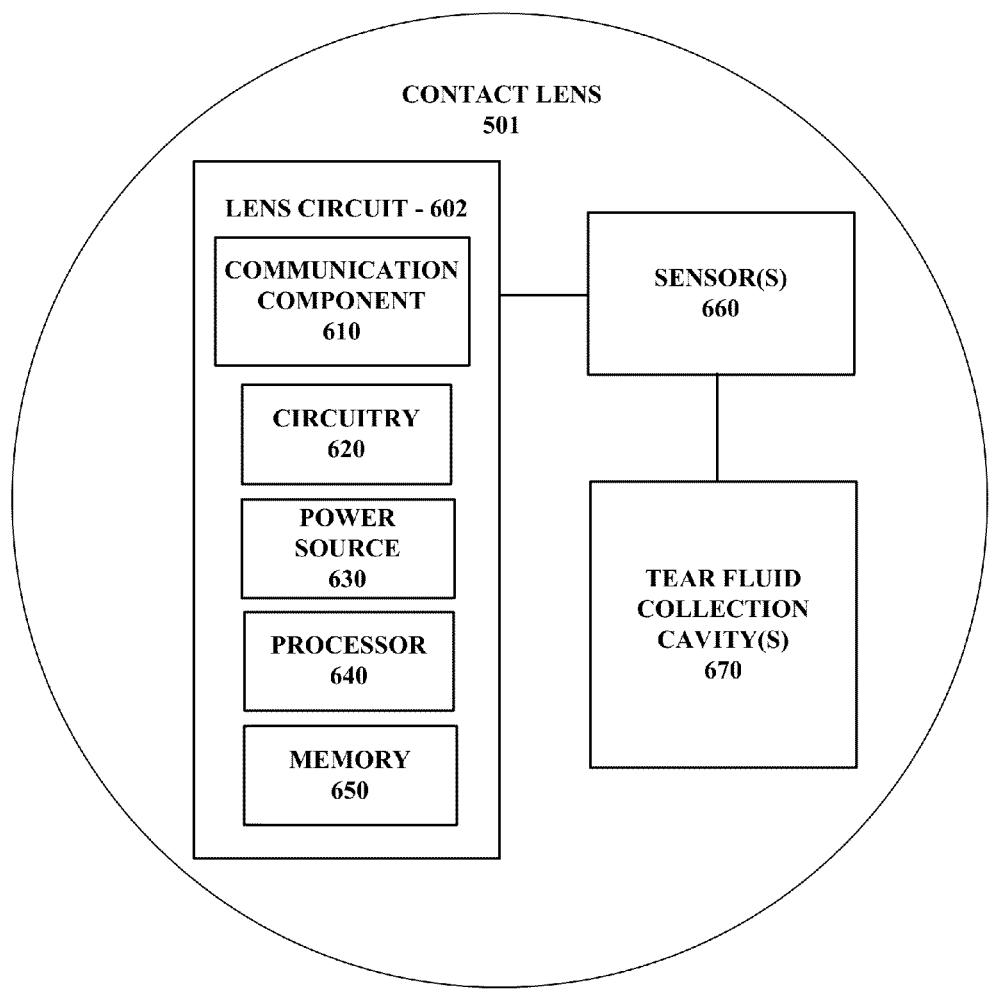
FIG. 6 is a high level illustration of an example contact lens circuit for employment in a contact lens to facilitate gathering, processing and wirelessly communicating, sensed information related to an analyte present in tear fluid collected in a cavity disposed within the contact lens, accordance with aspects described herein

FIG. 6 is a high level illustration of example contact lens that facilitates gathering, processing and wirelessly communicating, sensed information related to an analyte present in tear fluid collected in a cavity disposed within the contact lens, accordance with aspects described herein. Repetitive description of like elements employed in respective embodiments of contact lenses and contact lens circuits described herein is omitted for sake of brevity.

As shown in FIG. 6, contact lens 501 can include one or more sensors 660 and one or more tear fluid collection cavities 670. Contact lens 501 further includes contact lens circuit 602. Contact lens circuit can include communication component 610, circuitry 620, power source 630, processor 640, and memory 650. In various embodiments, one or more of the sensors 660, communication component 610, circuitry 620, power source 630, processor 640, and memory 650 can be electrically or chemically coupled to one another to perform one or more functions of the contact lens circuit 501. For example, one or more wires can connect the components of contact lens circuit 602 and the one or more sensors 660.

In an embodiment, aspects of contact lens circuit 602 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Contact lens circuit can include memory 650 for storing computer executable components and instructions. Processor 640 can facilitate operation of the computer executable components and instructions by contact lens circuit 602.

As discussed above, contact lens circuit can include a communication component 610 to facilitate sending and receiving wireless communications regarding sensing of an analyte within tear fluid collected in the one or more tear fluid collection cavities. For example, the communication component can include a receiver, a transmitter, a transceiver and/or a transducer. In an aspect, the communication component 610 includes an RF antenna that transmits and receives data regarding sensing of an analyte within tear fluid collected in the one or more tear fluid collection cavities.

In particular, the one or more sensors 660 are configured to sense information indicative of presence and/or concentration of an analyte of interest found within tear fluid collected in the one or more tear fluid collection cavities. Communication component 610 can include a transducer that converts sensed information (e.g. electrical signals) at the one or more sensors into a wireless transmittable signal representative of the sensed information. For example, where a sensor includes an electrochemical sensor, the sensed information can include an electrical signal having a voltage amplitude and/or time component representative of an amount of analyte present in tear fluid as determined over a period of time. The transducer and or a transmitter can further transmit the wireless signal to device external to contact lens 501 for processing thereof.

In an aspect, the communication component 610 can transmit information related to a sensed analyte in response to a request. According to this aspect, the communication component 610 can include a receiver that wirelessly receives a request for information related to a sensed analyte. The contact lens 501 can perform sensing of analytes in collected tear fluid and store any sensed information in memory. In response to a request, the transmitter can transmit requested information.

In various aspects, sensed signals captured by the one or more sensors 660 are wirelessly transmitted to an external device for subsequent processing thereof. However, in another aspect, contact lens circuit 602 performs on board processing of sensed signals. Accordingly rather than transmitting signals representative of raw data related to a sensed analyte (e.g. voltage amplitude signals generated by the one or more sensor where the one or more sensor are electrical sensors), processor 640 can process the raw data signals. In particular, processor can process signals generated by the one or more sensors to make various determinations and inferences based on the signals. In turn, communication component can transmit processed information relating to the various determinations or inferences.

In an aspect, processor 640 is configured to determine presence and/or concentration of a sensed analyte based on signals generate by the one or more sensors. In another aspect, processor 640 can determine changes in concentration of a sensed analyte over a period of time, such as throughout the day as the contact lens 501 is worn. Still in yet other aspect, processor 640 can determine and/or infer various health states of the wearer of the contact lens 501 based on a determined concentration of a sensed analyte.

In order to processes information generated by the one or more sensors, in an aspect, sensed signals can be stored in memory 650. Further, memory 650 can store various look-up tables and/or algorithms relating sensed information to analyte concentration and/or health states. For example, the look-up tables and/or algorithms can relate voltage amplitudes and durations to an analyte concentration, such as glucose. These algorithms and/or look-up tables can further relate analyte concentration, such as glucose concentration, to a health state, such as low blood sugar. In some aspects, where the one or more sensors 660 receive a steady flow of fresh tear fluid over the course of wear of contact lens 501 (e.g. as discussed with respect to FIG. 2A), memory 650 can store a log of the fluctuations in a sensed analyte throughout the course of the wear of the contact lens. According to this aspect, for example, memory can store a log of a wearer's glucose concentration. In turn, processor 640 can determine information related to fluctuations in a wearer's blood sugar level throughout the day.

In an embodiment, processor 640 can employ various (explicitly or implicitly trained) classification schemes or systems (e.g., support vector machines, neural networks, expert systems, Bayesian belief networks, fuzzy logic, data fusion engines, etc.) in connection with performing analysis of sensed signals at the one or more sensors 660. A classifier can map an input attribute vector, $x=(x1, x2, x3, x4 \ldots, xn)$, to a confidence that the input belongs to a class, such as by $f(x)$ =confidence(class). Such classification can employ a probabilistic or statistical-based analysis (e.g., factoring into the analysis utilities and costs) to prognose or infer a state of a retina. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Contact lens circuit 501 can additionally include the appropriate circuitry 6200 to facilitate the functions of contact lens circuit. For example, circuitry can facilitate the transfer of electrical responses received at the one or more sensor 660 to the communication component 610, memory 650, and/or processor 640. Circuitry 620 can also include signal processing hardware and software, (e.g. amplifiers, modulators, and etc.) for processing electrical signals received at the one or more sensor 660 for wireless transmission thereof.

Further, contact lens circuit 602 can include a power source 630. Power source 630 can include any suitable power source that can provide necessary power for the operation of various components of the contact lens circuit 602. For example, the power source 630 can include but is not limited to a battery, a capacitor, a solar power source, or a mechanically derived power source (e.g., MEMs system).

In an aspect, contact lens circuit 602 does not require an onboard (e.g. on the contact lens 501) power source to operate. In one aspect, contact lens circuit 602 can receive power via wireless energy transfer (e.g. using electromagnetic inductance techniques and related components).

Figure 7:
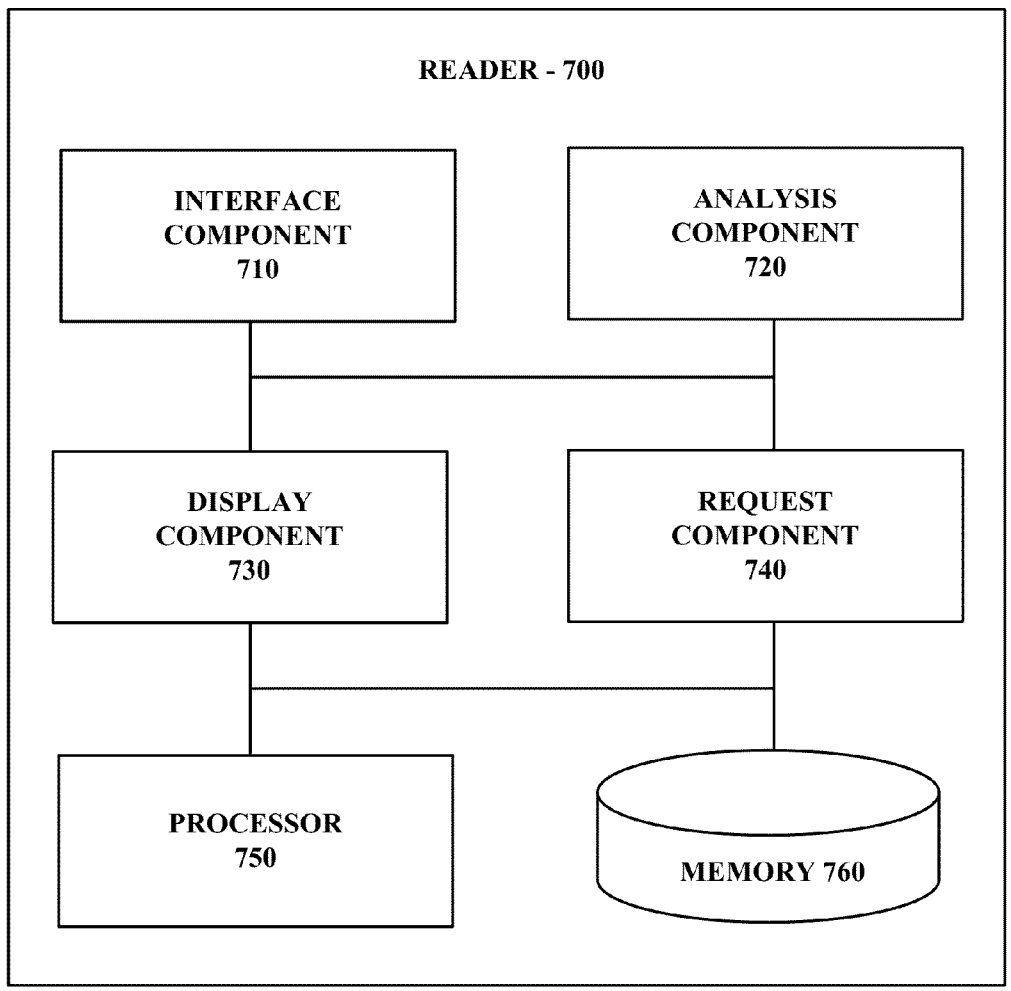
FIG. 7 presents an exemplary reader device for receiving, from a contact lens, information related to an analyte sensed in tear fluid collected by the contact lens in accordance with aspects described herein.

FIG. 7 is an illustration of an exemplary non-limiting reader device 700 that interfaces with a contact lens to receive information related to a sensed analyte in accordance with aspects described herein. In various aspects, the reader device 500 can include one or more of the structure and/or functionality of reader device 510 (and vice versa).

As shown in FIG. 7, reader device 700 can include interface component 710, analysis component 720, display component 730 and request component 740. Aspects of device 700 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Device 700 can include memory 760 for storing computer executable components and instructions. A processor 750 can facilitate operation of the computer executable components and instructions by device 700.

Interface component 710 interfaces with and receives from at least one contact lens, data relating to a sensed analyte. In particular, interface component 710 can interface with contact lenses described herein that comprise a contact lens circuit such as contact lens circuit 602 and the like. In an aspect, interface component 610 employs a receiving component, such as an RF receiver, transceiver, photodetector, or IR receiver, to receive sensed and/or determined information from a contact lens comprising a contact lens circuit as described herein. In some aspects, interfacing component 710 can receive determined or inferred information relating to concentration of a sensed analyte. According to this aspect, the contact lens can include appropriate circuitry and components to process data sensed by one or more sensors provided on or within the contact lens.

In another aspect, the reader can receive raw data from a contact lens relating to signals sensed at one or more sensor disposed within the contact lens. For example, the interface component 610 can receive signals indicating an amplitude and duration of an electrical signal generated by the one or more sensors. According to this embodiment, the reader 700 includes an analysis component 720 that can analyze received raw data to determine or infer information related to the sensed analyte.

Analysis component 720 can employ same or similar functionality described with reference to processor 640. In particular, analysis component 720 can determine and/or infer concentration of a sensed analyte and/or various health states of the wearer of the contact lens from which raw data information was transmitted based on a determined concentration of the sensed analyte. In order to processes information generated by the one or more sensors, in an aspect, received signals can be stored in memory 760. Further, memory 760 can store various look-up tables and/or algorithms relating sensed information to analyte concentration and/or health states.

Reader 700 can further include display component. In an aspect, display component generates a display corresponding to received sensor signals and/or determined or inferred analyte concentration/health state information. For example, display component 730 can include a display screen (e.g., a liquid crystal display screen (LCD)), that presents information to a user. For example, display component 730 can present a graphical display of fluctuation in concentration of a sensed analyte over course of wear of the contact lens. Reader 700 can further include request component 540 configured to generate a request for sensed analyte signals and/or determined or inferred information relating to sensed analyte signals. According to this aspect, the interface component 710 can include a transmitter that can transmit requests to the contact lens. In an aspect, the transmitter is an RF transmitter and transmits the instructions via a radio wave. According to this aspect, the instructions can include a data signal that can be received and interpreted by a contact lens communication component.

Figure 8:
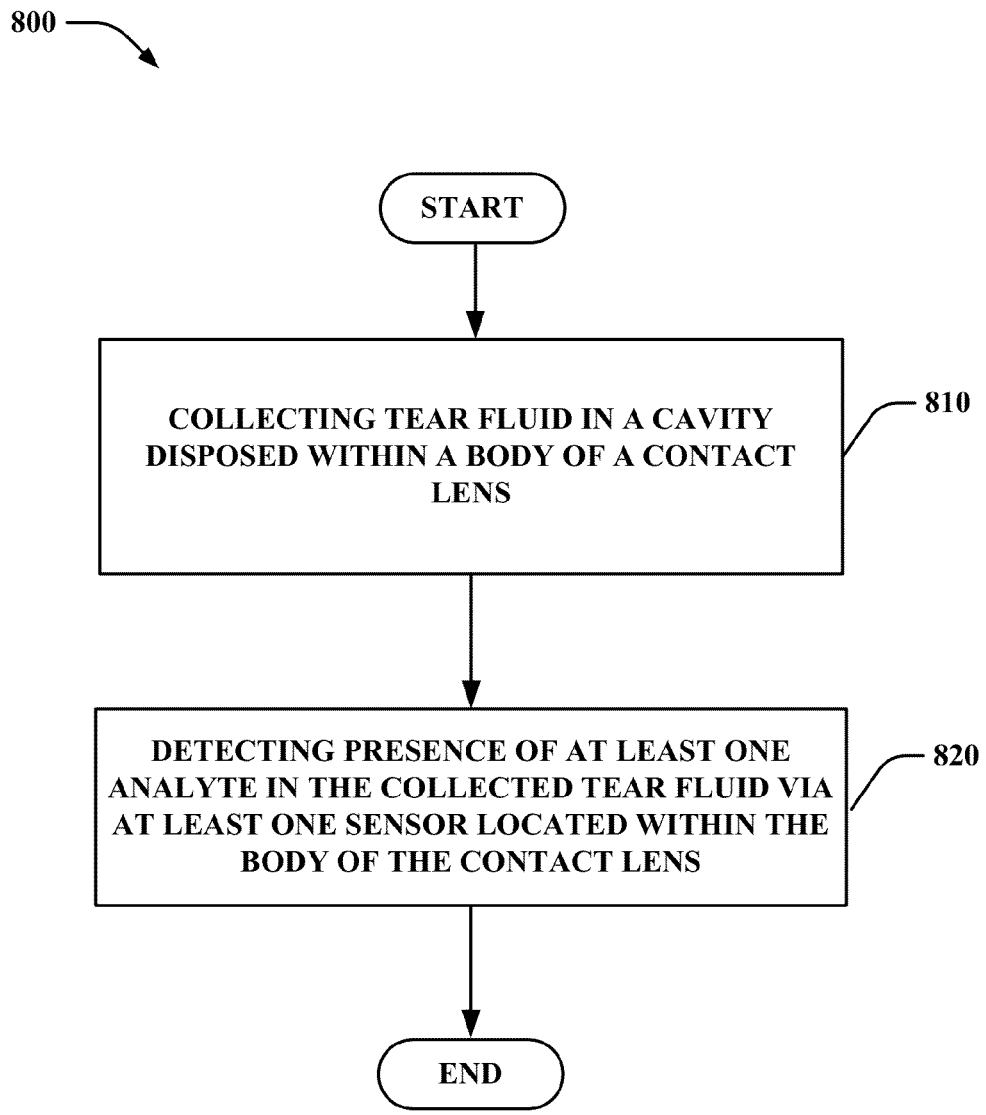
FIG. 8 is an exemplary flow diagram of a method that facilitates collecting tear fluid with a contact lens, and sensing an analyte in the collected tear fluid in accordance with aspects described herein.
Figure 9:
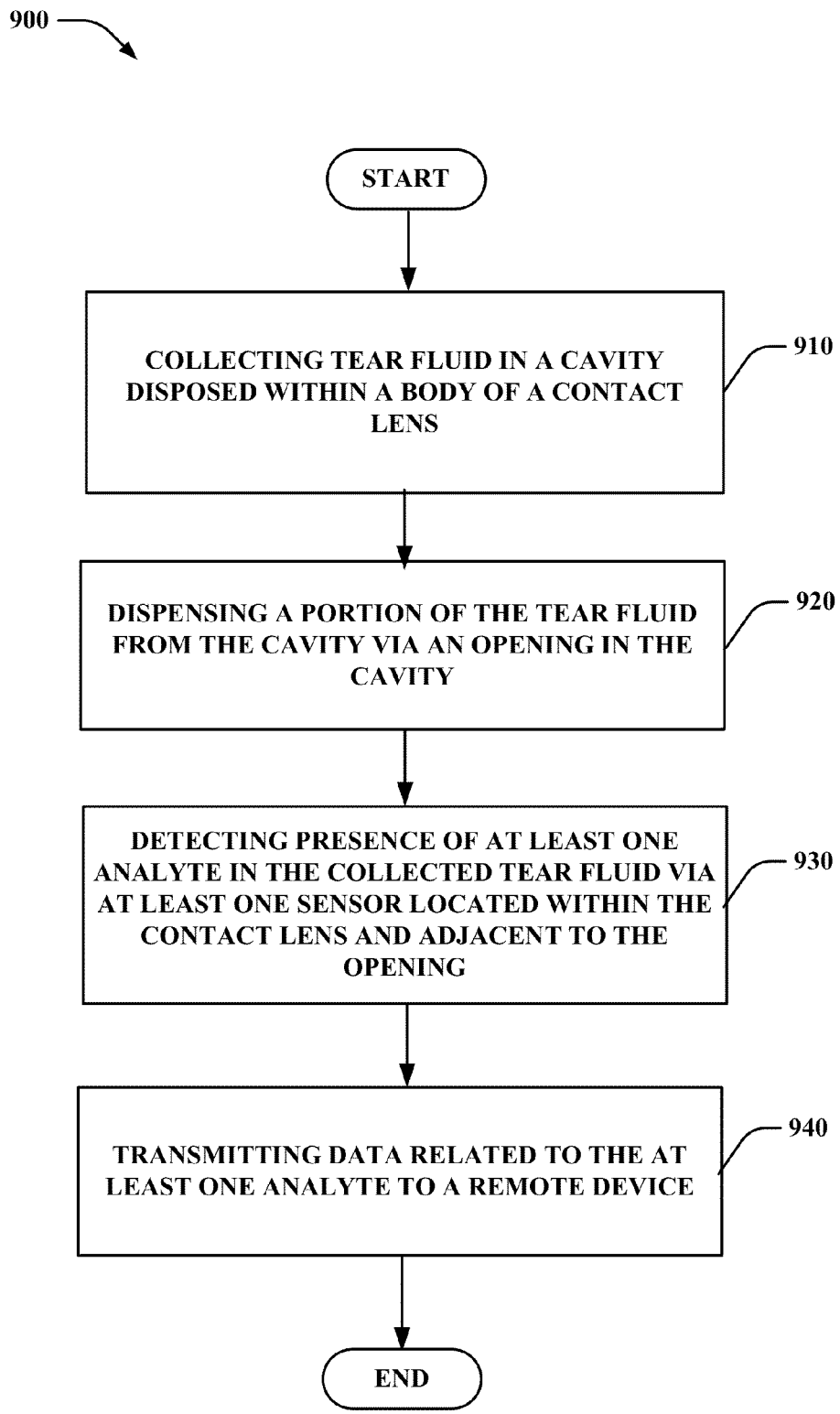
FIG. 9 is an exemplary flow diagram of a method that facilitates collecting tear fluid with a contact lens, sensing an analyte in the collected tear fluid, and transmitting information associated with the sensed analyte in accordance with aspects described herein.

FIGS. 8-9 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 8, presented is a flow diagram of an example application of systems and apparatuses disclosed in this description in accordance with an embodiment. In an aspect, in exemplary methodology 800, a contact lens such as those described herein (e.g. 501 and the like) is employed to sense information pertaining to an analyte concentration provided in collected tear fluid. At 810, tear fluid is collected in a cavity disposed within a bode of a contact lens (e.g., using tear fluid collection cavity 670). At 820, presence of the at least one analyte in the collected tear fluid is detected via at least one sensor located within the body of the contact lens (e.g., using sensor(s) 660).

Turning now to FIG. 9, presented is another flow diagram of an example application of systems and apparatuses disclosed in this description in accordance with an embodiment. In an aspect, in exemplary methodology 900, a contact lens such as those described herein (e.g., 501 and the like) is employed to sense information pertaining to an analyte concentration provided in collected tear fluid. At 910, tear fluid is collected in a cavity disposed within a bode of a contact lens (e.g., using tear fluid collection cavity 670). At 920, a portion of the tear fluid is dispensed for the cavity via an opening in the cavity. At 930, presence of the at least one analyte in the collected tear fluid is detected via at least one sensor located within the body of the contact lens and adjacent to the opening (e.g., using sensor(s) 660). At 940, data related to the at least one analyte is transmitted to a remote device (e.g., using communication component 610).

Exemplary Networked and Distributed Environments

Figure 10:
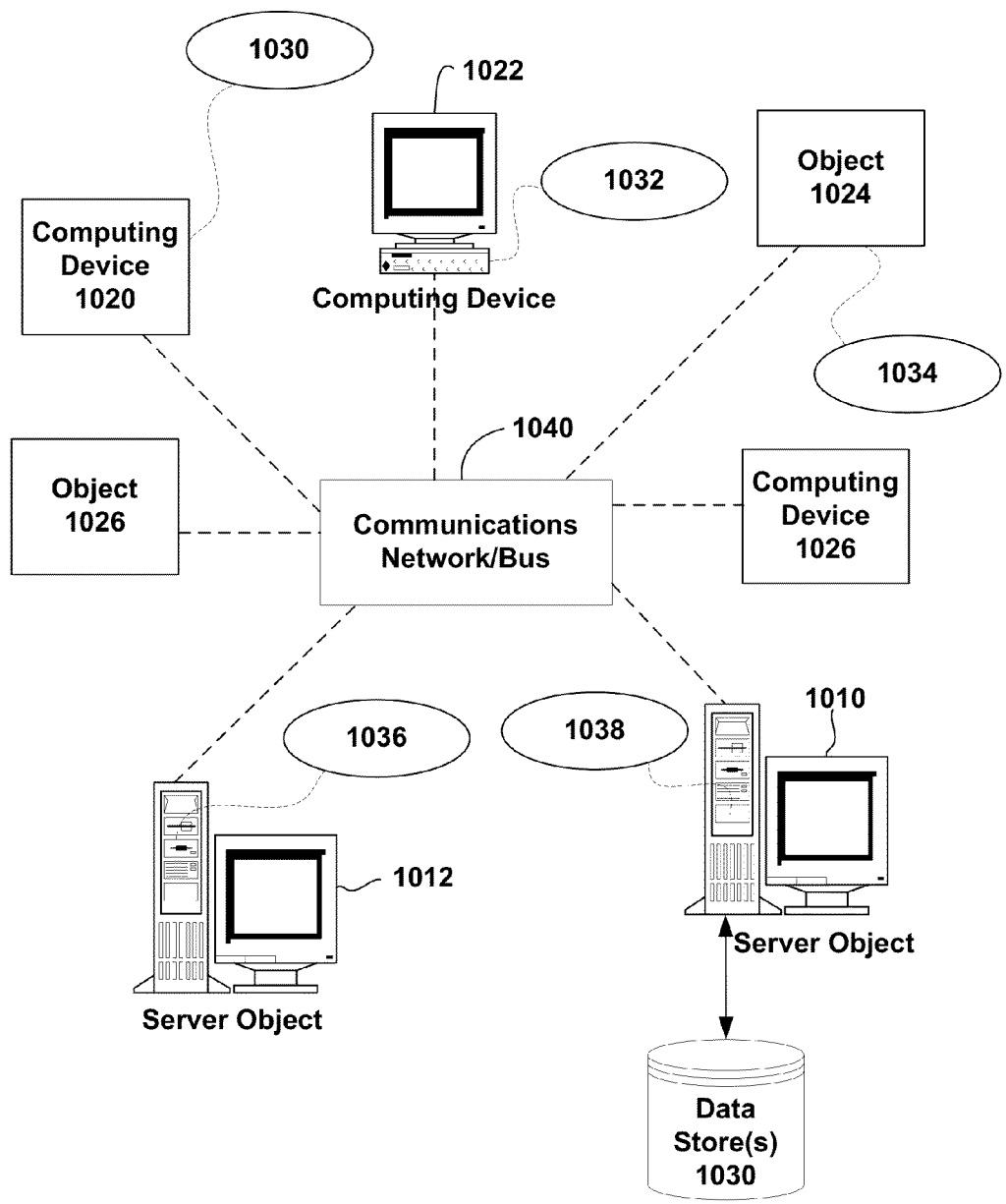
FIG. 10 is an illustration of a schematic diagram of an exemplary networked or distributed computing environment with which one or more aspects described herein can be associated.

FIG. 10 provides a schematic diagram of an exemplary networked or distributed computing environment with which one or more aspects described in this disclosure can be associated. The distributed computing environment includes computing objects 1010, 1012, etc. and computing objects or devices 1020, 1022, 1024, 1026, 1028, etc., which can include programs, methods, data stores, programmable logic, etc., as represented by applications 1030, 1032, 1034, 1036, 1038. It can be appreciated that computing objects 1010, 1012, etc. and computing objects or devices 1020, 1022, 1024, 1026, 1028, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 1010, 1012, etc. and computing objects or devices 1020, 1022, 1024, 1026, 1028, etc. can communicate with one or more other computing objects 1010, 1012, etc. and computing objects or devices 1020, 1022, 1024, 1026, 1028, etc. by way of the communications network 1040, either directly or indirectly. Even though illustrated as a single element in FIG. 10, network 1040 can include other computing objects and computing devices that provide services to the system of FIG. 10, and/or can represent multiple interconnected networks, which are not shown.

In a network environment in which the communications network/bus 1040 can be the Internet, the computing objects 1010, 1012, etc. can be Web servers, file servers, media servers, etc. with which the client computing objects or devices 1020, 1022, 1024, 1026, 1028, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or the reader described herein. In various aspects, the data store can include or be included within, any of the memory described herein, any of the contact lenses described herein and/or the reader device described herein. In various aspects, the data store can be any repository for storing information transmitted to or received from the contact lens.

Figure 11:
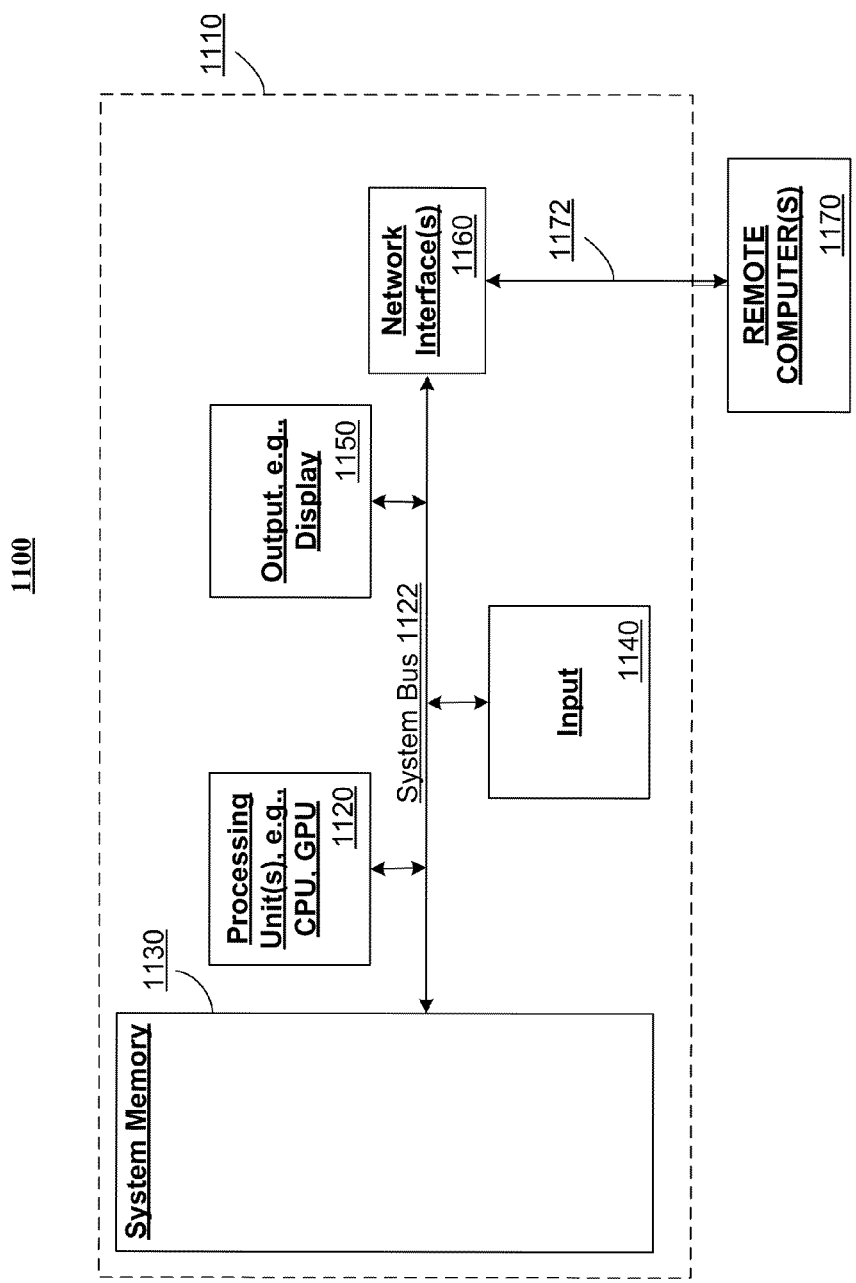
FIG. 11 is an illustration of a schematic diagram of an exemplary computing environment with which one or more aspects described herein can be associated.

FIG. 11 illustrates an example of a suitable computing system environment 1100 in which one or aspects of the aspects described in this disclosure can be implemented. Components of computer 1110 can include, but are not limited to, a processing unit 1120, a system memory 1130, and a system bus 1122 that couples various system components including the system memory to the processing unit 1120.

Computer 1110 typically includes a variety of computer readable media and can be any available media that can be accessed by computer 1110. The system memory 1130 can include computer storage media in the form of volatile and/or nonvolatile memory such as read only memory (ROM) and/or random access memory (RAM). By way of example, and not limitation, memory 1130 can also include an operating system, application programs, other program components, and program data.

A user can enter commands and information into the computer 1110 through input devices 1140 (e.g., keyboard, keypad, a pointing device, a mouse, stylus, touchpad, touch screen, motion detector, camera, microphone or any other device that allows the user to interact with the computer 1110). A monitor or other type of display device can be also connected to the system bus 1122 via an interface, such as output interface 1150. In addition to a monitor, computers can also include other peripheral output devices such as speakers and a printer, which can be connected through output interface 1150.

The computer 1110 can operate in a networked or distributed environment using logical connections to one or more other remote computers, such as remote computer 1160. The remote computer 1160 can be a personal computer, a server, a router, a network PC, a peer device or other common network node, or any other remote media consumption or transmission device, and can include any or all of the elements described above relative to the computer 1110. The logical connections depicted in FIG. 11 include a network 1170, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
   a substrate that forms at least part of a body of the contact lens, the contact lens having a concave surface and a convex surface opposite the concave surface, wherein the concave surface is configured to be removably mounted over a corneal surface of an eye;
   a plurality of recesses formed within the substrate and each of the plurality of recesses having an opening in the convex surface of the contact lens, configured to collect tear fluid when the contact lens is worn, and wherein each of the plurality of recesses extend into the body of the contact lens perpendicular to a line tangent to the convex surface at a center point of the convex surface; and
   at least one sensor disposed within the substrate configured to sense presence of an analyte in the collected tear fluid.

2. The contact lens of claim 1, wherein each of the plurality of recesses is formed at or about a perimeter of the contact lens.

3. The contact lens of claim 1, wherein each of the plurality of recesses has a depth spanning about a thickness of a cross-sectional area of the substrate.

4. The contact lens of claim 3, wherein each of the plurality of recesses has a depth within a range of about 50 to about 400 μm.

5. The contact lens of claim 1, wherein each of the plurality of recesses has a depth within a range of about 10 to about 75 μm.

6. The contact lens of claim 1, wherein the at least one sensor is located within at least one of the plurality of recesses.

7. The contact lens of claim 1, the at least one sensor is located adjacent to at least one of the plurality of recesses and wherein the at least one of the plurality of recesses includes an opening through which the tear fluid is dispensed and contacts the at least one sensor.

8. The contact lens of claim 1, wherein each of the plurality of recesses collects the tear fluid via capillary action.

9. The contact lens of claim 1, wherein the at least one sensor is an electrochemical sensor.

10. The contact lens of claim 1, comprising a transmitter configured to transmit data relating to a sensed analyte in the tear fluid.

11. The contact lens of claim 1, comprising a processor configured to determine a concentration of a sensed analyte in the tear fluid.

12. A method comprising:
   collecting tear fluid in a plurality of cavities disposed within a body of a contact lens, the contact lens having a concave surface and a convex surface opposite the concave surface, wherein the concave surface is configured to be removably mounted over a corneal surface of an eye, and each of the plurality of cavities having an opening in the convex surface of the contact lens, and wherein each of the plurality of cavities extends into the body of the contact lens perpendicular to a line tangent to the convex surface at a center point of the convex surface; and
   detecting presence of at least one analyte in the collected tear fluid via at least one sensor located within the body of the contact lens.

13. The method of claim 12, comprising transmitting data relating to a detected analyte in the tear fluid.

14. The method of claim 12, comprising determining a concentration of a sensed analyte in the tear fluid.

15. The method of claim 14, further comprising transmitting data related to the type or concentration of the sensed analyte to a remote device.

16. The method of claim 12, further comprising dispensing a portion of the tear fluid from at least one of the plurality of cavities via an opening so that the portion of the tear fluid contacts the at least one sensor.

17. The method of claim 12, wherein the collecting the tear fluid comprises collecting the tear fluid in the cavity via capillary action.

18. A contact lens, comprising:
a plurality of tear fluid collection recesses formed in a substrate that forms at least part of a body of the contact lens, the contact lens having a concave surface and a convex surface opposite the concave surface, wherein the concave surface is configured to be removably mounted over a corneal surface of an eye;
each of the plurality of recesses further having an opening in the convex surface of the contact lens and being configured to collect tear fluid when the contact lens is worn, and wherein each of the plurality of recesses extends into the body of the contact lens perpendicular to a line tangent to the convex surface at a center point of the convex surface;
at least one sensor configured to sense presence of one or more analytes in the tear fluid;
a processor configured to determine a concentration of the one or more analytes; and
a transmitter configured to transmit information relating to the concentration of the one or more analytes to an external device.

19. The contact lens of claim 18, further comprising a memory that stores information relating to the type or the concentration of the one or more analytes.

* * * * *